United States Patent [19]

Goble

[11] Patent Number: 5,385,567

[45] Date of Patent: Jan. 31, 1995

[54] SIGHT BARREL ARTHROSCOPIC INSTRUMENT

[76] Inventor: E. Marlowe Goble, 850 E. 1200 North, Logan, Utah 84321

[21] Appl. No.: 580,172

[22] Filed: Sep. 7, 1990

[51] Int. Cl.$^6$ .................... A61B 17/60; A61B 19/00
[52] U.S. Cl. ........................... 606/96; 606/86; 606/88; 606/89; 606/102
[58] Field of Search .......... 606/54, 60, 81–89, 606/96–98, 102–104, 88, 60, 97; 623/13

[56] References Cited

U.S. PATENT DOCUMENTS

| | | | |
|---|---|---|---|
| 3,727,611 | 4/1973 | Schultz | 606/86 |
| 4,627,425 | 12/1986 | Reese | 606/87 |
| 4,672,957 | 6/1987 | Hourehane | 606/96 |
| 4,823,780 | 4/1989 | Odensten et al. | 623/13 |
| 4,920,958 | 5/1990 | Walt et al. | 606/96 |

*Primary Examiner*—Randall L. Green
*Assistant Examiner*—P. Zuttarelli
*Attorney, Agent, or Firm*—M. Reid Russell

[57] ABSTRACT

A sight barrel arthroscopic instrument for use in a knee cruciate ligament repair procedure for forming a passage into the femoral endosteum to intersect, at an acute angle, a straight ligament tunnel that is formed from a point on the tibial tuberosity into the femur endosteum. Which instrument references the ligament tunnel to guide drilling of a passage from a point in the roof of the intercondyle notch to intersect the ligament tunnel in the femur endosteum, which passage is for receiving a fastener, such as a set screw, interference screw, or the like, that is installed into a ligament graft fitted in that ligament tunnel, providing an endosteal fixation of which ligament graft in that femur endosteum.

12 Claims, 2 Drawing Sheets

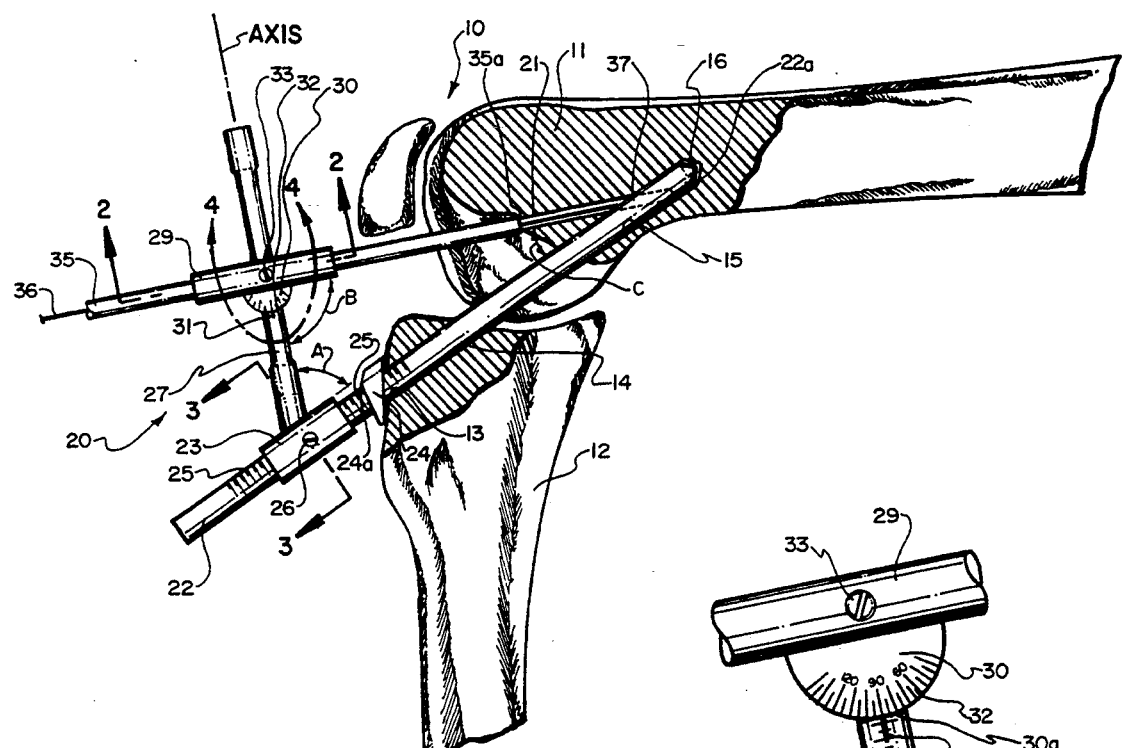
FIG. 1
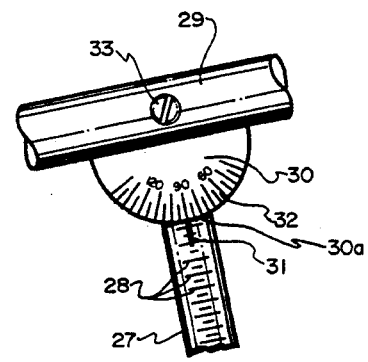
FIG. 4
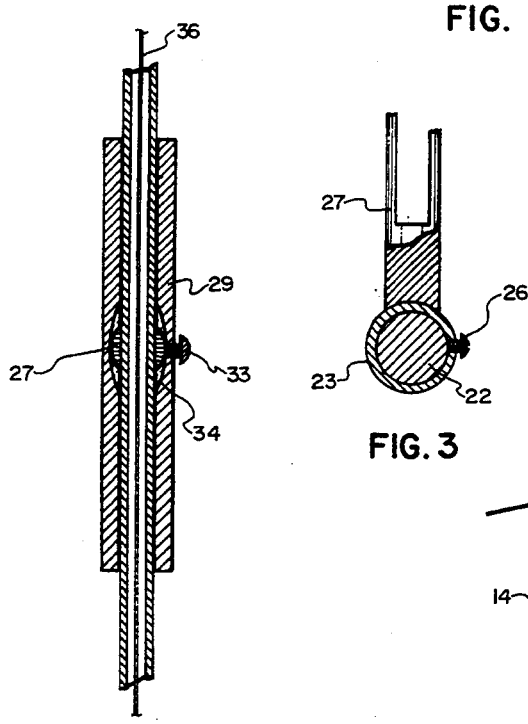
FIG. 2
FIG. 3
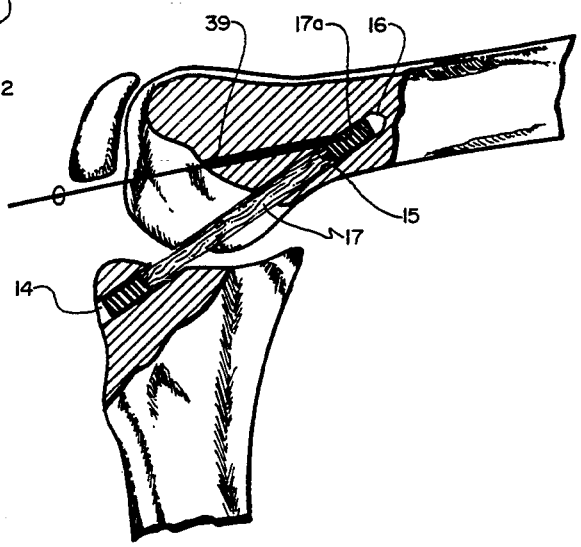
FIG. 5

SIGHT BARREL ARTHROSCOPIC INSTRUMENT

BACKGROUND OF THE INVENTION

1. Field of the Invention

This invention relates to surgical devices and in methods and in particularly to devices that are used in arthroscopic surgical procedures involving knee ligament reconstructive surgery.

2. Background

The present invention is in a arthroscopic surgical instrument and method for its use in a surgical procedure for replacement of an anterior cruciate ligament in tibial and femoral bony tunnel sections that, with the knee bent appropriately, form a straight tunnel. The ligament graft, for example, a bone-tendon-bone graft is to have one end secured endosteally in the femur endosteum with its other end placed in tension and is secured, as by stapling to the tibia anteromedial cortex. To provide this endosteal fixation in femur endosteum, the present invention provides a drill guide instrument for enabling a surgeon to form a passage from a point on the femur medial condyle notch to intersect the ligament tunnel in the femur endosteum. A fastener is then fitted through the formed passage to intersect and turn into the ligament end, providing a set screw type mounting of the ligament in the femur tunnel section. The present invention provides for aiming that passage to drill through a point on the roof of the intercondyle notch to exactly intersect the ligament graft end at a certain acute angle.

3. Prior Art

The present invention is utilized in arthroscopic surgical procedures for replacement of a knee cruciate ligament involving forming distal femur and proximal tibia bony tunnel sections that with the knee bent appropriately form a straight tunnel that receives a ligament secured therein. Such ligament replacement surgical procedure can involve drilling, from without the knee, a tunnel to intersect the formed ligament tunnel. The present inventor is a co-inventor of several drill guide inventions that perform this function. Specifically, a U.S. Pat. No. 4,901,711 and a U.S. patent application, Ser. No. 522743, that was filed on May 14, 1990, show drill guides for drilling from without the knee. Distinct therefrom the present invention provides for forming a passage within the intra-articular joint from a point on the roof of the intercondyle notch into the femur endosteum to intersect at a shallow acute angle, the femur section of the ligament tunnel. Wherethrough a set screw, or the like, can be fitted into a ligament end, such as a bone end of a bone tendon, bone, or the like, arranged therein, to endosteally secure that ligament end.

Additional to the patent and patent application set out above, the present inventor is the co-inventor of several patents that show a utilization of a straight bony tunnel in surgical procedures for repair or replacement of the anterior or posterior cruciate ligament. Such patents, for example include, "Ligament Anchor Attachment, Method and Apparatus" U.S. Pat. No. 4,772,286; "Ligament Attachment Anchor System" U.S. Pat. No. 4,870,957; a patent application entitled "Endosteal Fixation Stud and System" Ser. No. 465,914, filed Jan. 16, 1990, now U.S. Pat. No. 4,997,433. None of which patents, however, show a guide that is like the instrument of present invention.

Additional drilling systems for use in arthroscopic surgical procedures are shown in patents to: Sapeya et al, U.S. Pat. No. 4,739,751; Cho, U.S. Pat. No. 4,257,411; Hourahane et al, U.S. Pat. No. 4,535,768; Hourahane, U.S. Pat. No. 4,672,957; and a United Kingdom patent to Lovell et al, No. 2,078,528. All of which devices and arrangements provide for drilling from without the knee to a point in or around the intra-articular joint. Whereas, the present invention provides for forming a passage from a point within the intra-articular joint to intersect a ligament tunnel.

Functionally similar to the above cited patents, patents to Walt et al, U.S. Pat. No. 4,920,958; Purnell et al, U.S. Pat. No. 4,781,182; and Dunbar, IV, U.S. Pat. No. 4,708,139, also show drill guide arrangements for forming a hole from without a knee to a point in the intra-articular joint, as do patents to Seadholm et al, U.S. Pat. No. 4,668,223 and a European patent application No. 0126529.

Heretofore, within the knowledge of the inventor, there has not existed an instrument for guiding drilling by a surgeon to arthroscopically form a passage from a point on the roof of the intercondyle notch to exactly intersect a femoral tunnel section, which passage is for fitting a set screw, or like fastener, therein to endosteally secure the femoral end of a ligament graft within the femur endosteum.

SUMMARY OF THE INVENTION

It is a principal object of the present invention in a sight barrel arthroscopic instrument to provide a device and method for guiding drilling of a passage from a point in the roof of the intercondyle notch to intersect a predetermined point along a femoral tunnel section in a cruciate ligament replacement procedure, which passage is for receiving a set screw, or like attachment device, passed therethrough and turned into the end of a ligament graft seated in that femoral tunnel, endosteally securing that graft end.

Another object of the present invention is to provide an instrument for use in an arthroscopic cruciate ligament replacement surgical procedure that is minimal invasive, where the ligament graft end is endosteally secured in the femur endosteum by drilling from within the knee intra-articular joint to the femoral tunnel and fitting a set screw, or the like fastener in the ligament graft seated therein.

Still another object of the present invention is to provide an instrument for use in a arthroscopic surgical procedure for guiding drilling to exactly form a passage from a point on the distal femur to intersect, at an acute angle, a point along a femur section of a straight cruciate ligament tunnel.

Still another object of the present invention is to provide an instrument for use in an arthroscopic surgical procedure that is easy to use to accurately guide drilling of a passage from a point in the knee intra-articular joint to intersect a point along a femoral section, the passage for receiving a fastener fitting and turned therein into a ligament graft end, for endosteally securing that ligament graft end within the femur endosteum.

The sight barrel arthroscopic instrument of the present invention is for use in an arthroscopic surgical procedure for guiding drilling of a passage from within the knee intra-articular joint to intersect a straight cruciate ligament tunnel to a femur tunnel section. The intersecting passage is to receive a fastener, such as a set screw, turned therein and into a ligament graft end, such as a bone-tendon-bone graft, providing an endosteal mounting of the ligament graft.

The instrument includes a guide rod for fitting into the straight ligament tunnel with a mast extending outwardly therefrom. A sight barrel sleeve is mounted across the mast, which mast is set at an angle outwardly from the guide rod. The sight barrel sleeve is to receive a drill guide barrel telescoped therethrough to fit through an incision through a patient's knee below their patella and adjacent to the patellas tendon. The drill guide barrel slides through the incision to engage a point on the roof of the intercondyle notch. From that point the drill guide barrel guides a K-wire, or the like, telescoped therethrough and turned into the distal femur to exactly intersect, at an acute angle, a desired location along the femoral tunnel section in the femur endosteum. The drilled passage is for receiving a set screw, or the like fastener device, fitted and turned therealong into a ligament graft seated in the ligament tunnel, providing an endosteal attachment of that ligament graft end. Which ligament graft can be a bone-tendon-bone graft, or the like, the one bone end of which graft for receiving the set screw turned therein.

For locating an exact point or intersection point to the femoral tunnel, that may be the tunnel end, the sight barrel sleeve is arranged to be movable along the mast. For determining mast distance or length between the guide rod and sight barrel sleeve the mast includes spaced markings for alignment with an edge of the sight barrel sleeve. The sight barrel sleeve may be mounted at a fixed angle to the mast or may be pivotable with respect thereto. When such pivotally mounting is employed, the relative angle of which sight barrel sleeve to the mast can be determined by alignment of a vertical pointer scribed on which mast with a radial indicia scribed on an angle plate that is secured to which sight barrel sleeve. The radial indicia indicative of intervals of arc. So arranged, two angles of a triangle and one side are provided, and by trigonometric relationships the other two triangle sides and the acute angle of intersection are easily determined.

BRIEF DESCRIPTION OF THE DRAWINGS

These and other objects of the present invention will become more fully apparent from the following description, in which the invention is described in detail in conjunction with the accompanying drawings.

FIG. 1 shows a side elevation view of a patient's bent knee wherein a straight tunnel is formed from their tibial anteromedial cortex, through the anterior cruciate ligament points of origin, and into the femur endosteum, a guide rod of a sight barrel arthroscopic instrument of the invention is shown fitted in that straight tunnel, which guide rod includes a collar and has an upstanding mast extending therefrom whereon a sight barrel sleeve is mounted, forming a cross, which sight barrel sleeve receives a drill guide barrel telescoped therethrough, the end thereof engaging a point on the roof of the intercondyle notch, and showing a K-wire turned therethrough to a point along the femur tunnel section;

FIG. 2 is a sectional view taken along the line 2—2 of FIG. 1 showing an enlarged view of the sight barrel sleeve, drill guide barrel and K-wire;

FIG. 3 is a sectional view taken along the line 3—3 of FIG. 1 showing a sleeve mounting the mast telescoped over the guide rod;

FIG. 4 is an enlarged sectional view taken within the line 4—4 of FIG. 1, showing spaced lateral markings scribed at intervals along the mast and showing an angle plate mounted across the center of the sight barrel sleeve, showing indicia scribed thereon indicative of angles of arc and a pointer scribed on the mast for setting the angle of the sight barrel sleeve to the mast;

FIG. 5 shows a side elevation view of the knee showing a bone-tendon-bone ligament graft installed in the ligament tunnel with the K-wire shown drilled into the ligament graft bone end for endosteally securing that bone tendon bone graft within the ligament tunnel.

DETAILED DESCRIPTION OF THE INVENTION

Figure 6:
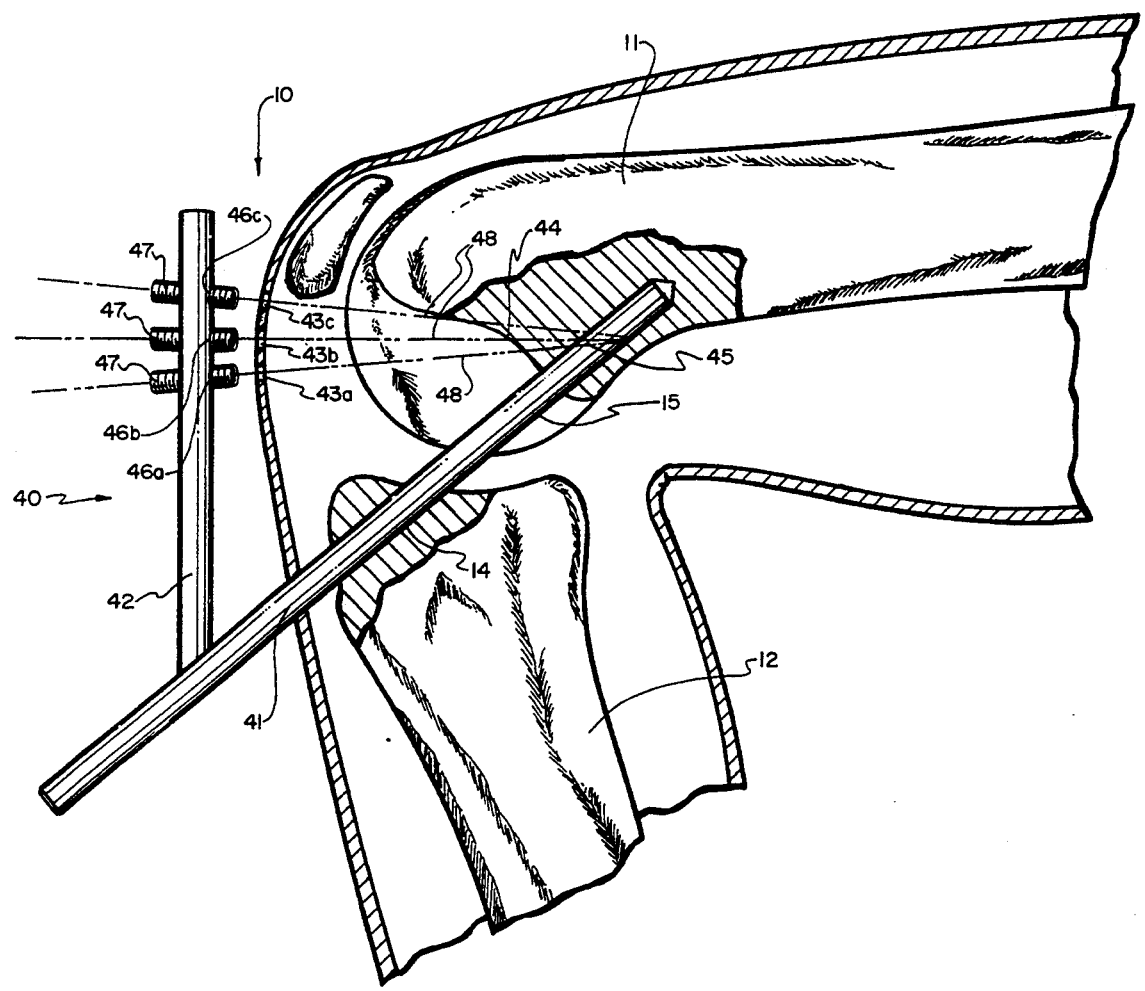
FIG. 6 is a side elevation view like that of FIG. 1 showing another embodiment of a sight barrel arthroscopic instrument of the invention.

FIG. 1 shows a side elevation view of a patient's bent knee 10 with sections of the distal femur 11 and proximal tibia 12 shown removed. A straight ligament tunnel is shown formed therein consisting of aligning tibial and femoral sections 14 and 15, respectively. The tibia section is shown formed from a point 13 on the tibial tuberosity, the tunnel extending through the points of origin of the anterior cruciate ligament and into the distal femur, terminating at end 16 in the femur endosteum.

The straight ligament tunnel formed by the tibial and femoral sections 14 and 15 is for receiving a prosthetic or natural ligament graft that is endosteally secured in the femoral section, the opposite ligament graft end extending from the proximal tibia open end 13 and is attached to the bone cortex, under appropriate tension, as by stapling or the like, to that tibia cortex surface. Or the graft end can be fixed within the tibial bony tunnel and is secured therein as with a bone-tendon-bone graft. An example of a ligament graft is shown in FIG. 5 as a bone-tendon-bone graft 17, that is shown being endosteally installed in the endosteum of the femoral section 15.

A sight barrel arthroscopic instrument 20, hereinafter referred to as "instrument" is shown in FIG. 1, installed to knee 10 for drilling a tunnel or passage from a point 21 located in the roof of the intercondyle notch to intersect, at an acute angle, the femoral section 15. Which intersection is preferably spaced a desired distance from the femur tunnel section end 16 and is for fitting a set screw, or the like, therein that is turned into the ligament graft end, endosteally locking that ligament end in the femur section endosteum.

In FIG. 1, the instrument 20 is shown as including guide rod 22, hereinafter referred to as "rod" whereon a sliding sleeve 23 and positioning collar 24 are telescoped. The rod 22 is for fitting into the straight ligament tunnel, either partially therein or to the end 16, as determined by the surgeon. In FIG. 1, the guide rod end 22a is shown closely proximate to the end 16 of the femoral tunnel section. After so installing the rod 22, the positioning collar 24 can be moved therealong into engagement with the tibia anteromedial cortex. As shown, the positioning collar 24 includes a flat face 24a that forms a right angle to the rod 22 for aligning with spaced markings 25 scribed on that rod 22 that are distance measurements in inches or millimeters, for determining the length of the rod within the femoral and tibial tunnels, taking into account for the thickness of collar 24. A surgeon, aligning the flat face 24a to a marking, can tell how far he has drilled into the femur endosteum.

As set out above and shown best in FIGS. 1 and 4, the sliding sleeve 23 is arranged to travel along the rod 22.

Which sleeve 23 includes a set screw 26, that as shown best in FIG. 3, is for turning into engagement with the rod 22 surface, releasably locking that sleeve thereto. To which sleeve 23 a mast 27 is shown secured. The mast extends therefrom at a certain angle A. Mast 27 like rod 22, preferably also includes spaced markings 28 scribed thereon for length reference to a sight barrel sleeve 29. The sight barrel sleeve 29 is arranged across and to travel vertically on which mast 27. An edge 30a of an angle gauge 30 that is secured to which sight barrel sleeve is used to align with one of the markings 28 for determining the spacing distance between the sliding sleeve 23 and sight barrel sleeve 29, taking into account the distance across which angle gauge to a lateral center of which sliding sleeve.

The sight barrel sleeve is shown herein arranged at approximately a ninety (90) degree angle B, to the mast 27. It should, however, be understood that the sight barrel sleeve 29 can be arranged to pivot on the mast 27, changing the angle B to greater or less than ninety (90) degrees. For this application, to measure this angle, the angle gauge 30 is shown secured across the sight barrel sleeve 29 at its junction with the mast 27. Which mast includes a pointer 31 scribed centrally and longitudinally thereon whose end is for pointing at one of the radial indices of angles 32 scribed thereon, for determining angle B. So arranged, the angle A between the sliding sleeve 23 and rod 22 is set, the distance between the sliding and sight barrel sleeves 23 and 27, taking into account the width of the angle gauge, can be determined by aligning the edge 30a of the angle gauge 30 over a mast marking 28. The angle B is either set at ninety (90) degrees or can be determined by aligning of the mast arrow 31 end with an angle marking on the angle gauge 30 and reading the angle off from the angle gauge. Which angle gauge 30 is shown as a plate with radial markings scribed thereon that emanate from the center of the intersection of the lateral center of the sight barrel sleeve and mast, which radial markings are indicative of angles of arc.

FIG. 2 shows the sight barrel sleeve 29 as including a set screw 33 that is for turning into engagement with the mast 27, locking the two together. If the angle between the sight barrel sleeve and mast is to be adjustable, rotation of the sight barrel sleeve 29 relative to the mast 27, must be provided for. Accordingly, a hole 34 wherethrough the mast 27 is fitted is shown as being slightly elliptical to accommodate such rotation.

Shown in FIGS. 1, 2 and 5, the sight barrel sleeve 29 receives a drill guide barrel 35 telescoped therethrough that in turn, a K-wire 36 is shown fitted through. The end 35a of which drill guide barrel is shown positioned against point 21 on the roof of the intercondyle notch. The K-wire is shown turned through that point into the femoral endosteum to intersect the femur section 15 of the ligament tunnel, and rod 22, at an acute angle C. This acute angle C can, of course, be determined by subtracting the sum of the angles A and B from one hundred eighty (180) degrees, the remainder being acute angle C.

If angle B is a right angle the distance along the rod 22(r) and with the distance between sleeves 23 and 27(x) known, the length of the rod 22 to the intersection with the K-wire 36 is determined from the formula:

$$\text{cosine (cos) } B = x \text{ and } r = \frac{x}{\cos B}. \quad (1)$$

If angle A is not a right angle, with acute angle C determined as:

$$\text{acute angle } C = 180° - A - B;$$

r can be determined by solving:

$$\frac{x + r}{x - r} = \frac{\tan 1/2 \text{ (angles } C + B)}{\tan 1/2 \text{ (angles } C - B)}. \quad (2)$$

From one of the formulas (1) or (2) above, intersection point 37 and the acute angle C of intersection of the K-wire to the femoral tunnel side can be determined. Which intersection can also be seen on a fluoroscopic monitor, or like monitor, as may be used by a surgeon performing an arthroscopic procedure. The surgeon, by determining the angles A and B and side x can thereby exactly determine the angle C and intersection point 37 on the femoral tunnel that the K-wire intersects. All of which angles and distances can be set out in a chart constituted from the above formulas for convenient operating room use.

A connection device, such as the K-wire that has been cut off appropriately, a set screw, converging interference screw, or the like, not shown, can be fitted through the passage formed by the K-wire 36 to intersect and enter that ligament end, as shown in FIG. 5. An endosteal fixation of a ligament 17, end 17a, shown as a bone end of a bone-tendon-bone graft is thereby provided. The withdrawal of the bone end 17a of the graft 17 from the femur endosteum is thereby provided.

This invention as described hereinabove involves a sight barrel sleeve 29 that is either maintained in a right angle relationship to the mast 27, or, the angle between these components could be arranged to be st at less or greater than ninety (90) degrees. Further, the distance (x) between the sleeve 23 and sight barrel sleeve 29 could also be fixed, within the scope of this disclosure. In such arrangement, where angles A and B are fixed as is the distance (x) a set point or location of intersection with the femoral tunnel section is provided. Also, as set out above, a surgeon does not have time to utilize the formulas (1) and (2), and accordingly, a chart setting up the angular relationships, the lengths of the drilled distance, and the length of the ligament tunnel to the intersection can be prepared as a convenient graph that is easily and quickly referred to by a surgeon, nurse or the like for determining angles and lengths during the procedure.

Additionally, shown in FIG. 6, is another embodiment of a sight barrel arthroscopic instrument 40 of the invention, hereinafter referred to as "instrument". Like instrument 20, instrument 40 includes a guide rod 41, hereinafter referred to as "rod" and a mast 42 that extends upwardly therefrom. Distinct from instrument 20, instrument 40 provides for drilling through different skin portals 43a, 43b and 43c to and through an area 44 on the roof of the intercondyle notch to intersect the femur tunnel section 15 at approximately a same point 45. This capability is provided by formation of vertically spaced passages 46a, 46b an 46c through mast 42, which may be tapped or otherwise arranged to receive and mount a cannulated guide 47, shown as tubes fitted therethrough to guide turning of a K-wire 48, or the like therethrough. A cannulated guide 47 can be fitted in a select passage 46a, 46b or 46c, or a cannulated guide can be provided for each passage. So arranged, instrument 40 provides for drilling a passage to intersect essentially a same point 45 from different skin portals 43a, 43b and 43c for accommodating different knee conditions as may exist.

While preferred embodiments of the present invention in a sight barrel arthroscopic instrument and method for its use have been shown and described herein, it should however, be apparent that this disclosure is made by way of example only and that variations and modifications to the instruments and their use are possible within the scope of this disclosure without departing from the subject matter coming within the scope of the following claims and reasonable equivalency thereof, which claims I regard as my invention.

I claim:

1. A sight barrel arthroscopic instrument comprising, a guide rod for fitting in a straight cruciate ligament tunnel formed in a patient's knee from the tibial tuberosity through the ligament points of origin and into the femur endosteum; a straight mast secured to said guide rod, to extend vertically therefrom in alignment with the vertical plane of and spaced apart from the patient's knee when said guide rod is positioned in the straight cruciate ligament tunnel; and a sight barrel sleeve means for mounting across and spaced a distance along said straight mast from said guide rod, and is for guiding drilling of an intersecting tunnel from outside the knee in the vertical plane in front of the knee to a point along the distal femur intracondyle notch and into the femur endosteum, to intersect, at an acute angle, the straight cruciate ligament tunnel.

2. A sight barrel arthroscopic instrument as recited in claim 1, further including a collar for sliding along the guide rod to engage the tibial tuberosity at the end of the ligament tunnel; spaced markings at intervals along said guide rod; and means for locking the straight mast to the guide rod.

3. A sight barrel arthroscopic instrument as recited in claim 1, wherein the straight mast is mounted to extend from a sleeve that is releasably secured to the guide rod; and set screw means extending through a wall of said sleeve for turning to engage said guide rod.

4. A sight barrel arthroscopic instrument as recited in claim 1, wherein the sight barrel sleeve means is a single sleeve mounted so as to be adjustable along the straight mast; and the straight mast has spaced marking therealong for determining the distance between the guide rod and said sight barrel sleeve means.

5. A sight barrel arthroscopic instrument as recited in claim 4, wherein the single sleeve is pivotally mounted across the straight mast; and means for determining the angle of said single sleeve to said mast.

6. A sight barrel arthroscopic instrument as recited in claim 5, wherein the means for determining the angle is an angle gauge with radial markings thereon indicative of angles of arc; and a longitudinal pointer is centered on the straight mast, the one pointer end for aligning with one of the radial markings of the angle gauge, indicating the relative angle between said sight barrel sleeve and mast.

7. A sight barrel arthroscopic instrument as recited in claim 1, wherein the sight barrel sleeve means is a plurality of sleeve mounting each sleeve mounting for fitting through one of a plurality of spaced holes formed through the straight mast.

8. A sight barrel arthroscopic instrument as recited in claim 7, wherein the individual sleeve mountings are each cannulated and are each threaded externally for turning in one of the spaced holes that are tapped to receive each said individual sleeve turned therein.

9. A sight barrel arthroscopic instrument as recited in claim 7, where the sleeve mountings to the straight mast are angled with respect to the straight mast such that the longitudinal axis of which sleeves converge at the femoral section of the straight ligament tunnel.

10. A sight barrel arthroscopic instrument as recited in claim 1, further including a drill guide barrel for telescoping through the sight barrel sleeve means, one end of said drill guide barrel to intersect a point on the distal femur intracondyle notch.

11. A sight barrel arthroscopic instrument as recited in claim 10, wherein the drill guide barrel is to receive and guide a drill means turned therethrough and into the distal femur.

12. A sight barrel arthroscopic instrument as recited in claim 11, wherein the drill means is a K-wire.

* * * * *